United States Patent
Zakariaie et al.

(10) Patent No.: US 11,640,572 B2
(45) Date of Patent: May 2, 2023

(54) OCULAR SYSTEM TO OPTIMIZE LEARNING

(71) Applicant: Senseye, Inc., Austin, TX (US)

(72) Inventors: David Zakariaie, Austin, TX (US); Kathryn McNeil, Austin, TX (US); Alexander Rowe, Austin, TX (US); Joseph Brown, Austin, TX (US); Patricia Herrmann, Austin, TX (US); Jared Bowden, Austin, TX (US); Taumer Anabtawi, Austin, TX (US); Andrew R. Sommerlot, Austin, TX (US); Seth Weisberg, Austin, TX (US); Veronica Choi, Austin, TX (US)

(73) Assignee: Senseye, Inc., Austin, TX (US)

( * ) Notice: Subject to any disclaimer, the term of this patent is extended or adjusted under 35 U.S.C. 154(b) by 196 days.

(21) Appl. No.: 17/247,636

(22) Filed: Dec. 18, 2020

(65) Prior Publication Data
US 2021/0192351 A1    Jun. 24, 2021

Related U.S. Application Data

(60) Provisional application No. 62/950,918, filed on Dec. 19, 2019.

(51) Int. Cl.
*G06K 9/62* (2022.01)
*G06N 3/08* (2023.01)
(Continued)

(52) U.S. Cl.
CPC ............ *G06N 3/08* (2013.01); *A61B 3/0025* (2013.01); *A61B 3/0041* (2013.01);
(Continued)

(58) Field of Classification Search
CPC ........ G06N 3/08; G06N 3/0454; G06N 3/088; G06N 3/0472; A61B 3/0025;
(Continued)

(56) References Cited

U.S. PATENT DOCUMENTS 7,614,745 B2    11/2009    Waldorf et al.
9,357,918 B1    6/2016    Cohen
(Continued)

FOREIGN PATENT DOCUMENTS

CN    106796449 A  *  5/2017  ............. A61B 3/113
CN    111081371 A  *  4/2020
(Continued)

OTHER PUBLICATIONS

Alexander, M. P., D. T. Stuss, and N. Fansabedian. "California Verbal Learning Test: Performance by Patients with Focal Frontal and Non-frontal Lesions." Brain 126, No. 6 (Jun. 1, 2003): 1493-1503. https://doi.org/10.1093/brain/awg128.
(Continued)

*Primary Examiner* — Xin Jia
(74) *Attorney, Agent, or Firm* — Orbit IP

(57) ABSTRACT

A method to optimize learning based upon ocular information of a subject includes providing a video camera for recording a close-up view of a subject's eye. A first electronic display shows a plurality of educational subject matter to the subject. A second electronic display shows an output to an instructor. Changes in ocular signals of the subject are processed through the use optimized algorithms. A cognitive state model determines a low to a high cognitive load experienced by the subject. The cognitive state model is evaluated based on the changes in the ocular signals for determining a probability of the low to the high cognitive
(Continued)

load experienced by the subject. The probability of the low to the high cognitive load experienced by the subject is displayed to the instructor.

7 Claims, 8 Drawing Sheets

(51) Int. Cl.

| | | |
|---|---|---|
| G06T 7/73 | (2017.01) | |
| A61B 5/16 | (2006.01) | |
| G16H 50/50 | (2018.01) | |
| G16H 30/20 | (2018.01) | |
| G16H 50/70 | (2018.01) | |
| G16H 50/20 | (2018.01) | |
| A61B 3/00 | (2006.01) | |
| A61B 3/14 | (2006.01) | |
| A61B 5/00 | (2006.01) | |
| G06N 3/04 | (2023.01) | |
| A61B 3/11 | (2006.01) | |
| G16H 15/00 | (2018.01) | |
| A61B 3/113 | (2006.01) | |
| A61B 5/11 | (2006.01) | |
| G06Q 10/0635 | (2023.01) | |
| G06Q 10/0639 | (2023.01) | |
| G06Q 10/10 | (2023.01) | |
| G06V 20/40 | (2022.01) | |
| G06V 40/18 | (2022.01) | |
| G06V 40/19 | (2022.01) | |
| G16H 50/30 | (2018.01) | |
| G06N 3/088 | (2023.01) | |

(52) U.S. Cl.
CPC ............ *A61B 3/0091* (2013.01); *A61B 3/112* (2013.01); *A61B 3/113* (2013.01); *A61B 3/145* (2013.01); *A61B 5/1103* (2013.01); *A61B 5/161* (2013.01); *A61B 5/163* (2017.08); *A61B 5/165* (2013.01); *A61B 5/4845* (2013.01); *A61B 5/4863* (2013.01); *A61B 5/6898* (2013.01); *A61B 5/7246* (2013.01); *G06N 3/0454* (2013.01); *G06Q 10/0635* (2013.01); *G06Q 10/06398* (2013.01); *G06Q 10/10* (2013.01); *G06T 7/73* (2017.01); *G06V 20/46* (2022.01); *G06V 40/18* (2022.01); *G06V 40/19* (2022.01); *G16H 15/00* (2018.01); *G16H 30/20* (2018.01); *G16H 50/20* (2018.01); *G16H 50/50* (2018.01); *G16H 50/70* (2018.01); *A61B 5/7267* (2013.01); *A61B 2503/20* (2013.01); *G06N 3/088* (2013.01); *G06T 2207/10016* (2013.01); *G06T 2207/20081* (2013.01); *G06T 2207/20084* (2013.01); *G06T 2207/30041* (2013.01); *G16H 50/30* (2018.01)

(58) Field of Classification Search
CPC ..... A61B 3/0041; A61B 3/0091; A61B 3/112; A61B 3/113; A61B 3/145; A61B 5/1103; A61B 5/161; A61B 5/163; A61B 5/165; A61B 5/4845; A61B 5/4863; A61B 5/6898; A61B 5/7246; A61B 5/7267; A61B 2503/20; A61B 3/14; A61B 5/0077; A61B 5/164; G06Q 10/0635; G06Q 10/06398; G06Q 10/10; G06T 7/73; G06T 2207/10016; G06T 2207/20081; G06T 2207/20084; G06T 2207/30041; G06V 20/46; G06V 40/18; G06V 40/19; G06V 10/143; G06V 10/454; G06V 10/764; G06V 40/193; G16H 15/00; G16H 30/20; G16H 50/20; G16H 50/50; G16H 50/70; G16H 50/30; G16H 10/20; G16H 20/70; G16H 30/40

See application file for complete search history.

(56) References Cited

U.S. PATENT DOCUMENTS

| | | | |
|---|---|---|---|
| 9,357,966 B1 | 6/2016 | Cohen | |
| 9,953,650 B1* | 4/2018 | Falevsky | ................ G06F 3/013 |
| 2004/0174496 A1 | 9/2004 | Ji et al. | |
| 2009/0216092 A1 | 8/2009 | Waldorf et al. | |
| 2011/0066082 A1 | 3/2011 | Duffy | |
| 2014/0178843 A1 | 6/2014 | Smyth | |
| 2015/0338915 A1* | 11/2015 | Publicover | ........... G06V 40/197 |
| | | | 345/633 |
| 2018/0160959 A1 | 6/2018 | Wilde et al. | |

FOREIGN PATENT DOCUMENTS

| | | | |
|---|---|---|---|
| CN | 111191573 A | * | 5/2020 |
| JP | 2006 525829 A | | 11/2006 |
| UA | 116785 U | | 6/2017 |
| WO | 2007 131076 A2 | | 11/2007 |

OTHER PUBLICATIONS

Anderson, Kristen Joan. "Impulsitivity, Caffeine, and Task Difficulty: A within-Subjects Test of the Yerkes-Dodson Law." Personality and Individual Differences 16, No. 6 (Jun. 1, 1994): 813-29. https://doi.org/10.1016/0191-8869(94)90226-7.

Chaby, Lauren E, Michael J Sheriff, Amy M Hirrlinger, and Victoria A Braithwaite. "Can We Understand How Developmental Stress Enhances Performance under Future Threat with the Yerkes-Dodson Law?" Communicative & Integrative Biology 8, No. 3 (Jul. 6, 2015): e1029689-e1029689. https://doi.org/10.1080/19420889.2015.1029689.

Cohen, N. J., and H. Eichenbaum. "Memory, Amnesia, and the Hippocampal System. 1993." Cambridge, MA: MIT Press 3 (1993): 285-290.

Dimitrov, Mariana, Joy Granetz, Matthew Peterson, Caroline Hollnagel, Gene Alexander, and Jordan Grafman. "Associative Learning Impairments in Patients with Frontal Lobe Damage." Brain and Cognition 41, No. 2 (Nov. 1, 1999): 213-30. https://doi.org/10.1006/brcg.1999.1121.

Ebitz, R. Becket, and Tirin Moore. "Selective Modulation of the Pupil Light Reflex by Microstimulation of Prefrontal Cortex." The Journal of Neuroscience 37, No. 19 (May 10, 2017): 5008. https://doi.org/10.1523/JNEUROSCI.2433-16.2017.

Eslinger, Paul J., and Lynn M. Grattan. "Altered Serial Position Learning after Frontal Lobe Lesion." Neuropsychologia 32, No. 6 (Jun. 1, 1994): 729-39. https://doi.org/10.1016/0028-3932(94)90032-9.

Hampson, R.E., Ioan Opris, and S.A. Deadwyler. "Neural Correlates of Fast Pupil Dilation in Nonhuman Primates: Relation to Behavioral Performance and Cognitive Workload." Behavioural Brain Research 212, No. 1 (Sep. 1, 2010): 1-11. https://doi.org/10.1016/j.bbr.2010.03.011.

Jetter, Wolfgang, Ulrich Poser, Robert B. Freeman, and Hans J. Markowitsch. "A Verbal Long Term Memory Deficit in Frontal Lobe Damaged Patients." Cortex 22, No. 2 (Jun. 1, 1986): 229-42. https://doi.org/10.1016/S0010-9452(86)80047-8.

Jonides, John, Richard L Lewis, Derek Evan Nee, Cindy A Lustig, Marc G Berman, and Katherine Sledge Moore. "The Mind and Brain of Short-Term Memory." Annual Review of Psychology 59 (2008): 193-224. https://doi.org/10.1146/annurev.psych.59.103006.093615.

Joshi, Siddhartha, Yin Li, Rishi M. Kalwani, and Joshua I. Gold. "Relationships between Pupil Diameter and Neuronal Activity in

(56) References Cited

OTHER PUBLICATIONS the Locus Coeruleus, Colliculi, and Cingulate Cortex." Neuron 89, No. 1 (Jan. 6, 2016): 221-34. https://doi.org/10.1016/j.neuron.2015.11.028.

Kesner, Raymond P., Ramona O. Hopkins, and Bonnie Fineman. "Item and Order Dissociation in Humans with Prefrontal Cortex Damage." Neuropsychologia 32, No. 8 (Aug. 1, 1994): 881-91. https://doi.org/10.1016/0028-3932(94)90040-X.

Kucewicz, Michal T., Jaromir Dolezal, Vaclav Kremen, Brent M. Berry, Laura R. Miller, Abigail L. Magee, Vratislav Fabian, and Gregory A. Worrell. "Pupil Size Reflects Successful Encoding and Recall of Memory in Humans." Scientific Reports 8, No. 1 (Mar. 21, 2018): 4949. https://doi.org/10.1038/s41598-018-23197-6.

McAndrews, Mary Pat, and Brenda Milner. "The Frontal Cortex and Memory for Temporal Order." Neuropsychologia 29, No. 9 (Jan. 1, 1991): 849-59. https://doi.org/10.1016/0028-3932(91)90051-9.

Moscovitch, Morris, and Gordon Winocur. "Frontal Lobes, Memory, and Aging." Annals of the New York Academy of Sciences 769, No. 1 (Dec. 1, 1995): 119-50. https://doi.org/10.1111/j.1749-6632.1995.tb38135.x.

Nakayama, Minoru, and Yasutaka Shimizu. "Frequency Analysis of Task Evoked Pupillary Response and Eye-Movement." In Proceedings of the 2004 Symposium on Eye Tracking Research & Applications, 71-76. San Antonio, Texas: ACM, 2004.

Peysakhovich, Vsevolod, Mickael Causse, Sébastien Scannella, and Frédéric Dehais. "Frequency Analysis of a Task-Evoked Pupillary Response: Luminance-Independent Measure of Mental Effort." International Journal of Psychophysiology 97, No. 1 (Jul. 1, 2015): 30-37. https://doi.org/10.1016/j.ijpsycho.2015.04.019.

Peysakhovich, Vsevolod, Francois Vachon, and Frédéric Dehais. "The Impact of Luminance on Tonic and Phasic Pupillary Responses to Sustained Cognitive Load." International Journal of Psychophysiology 112 (Feb. 1, 2017): 40-45. https://doi.org/10.1016/j.ijpsycho.2016.12.003.

Reiner, Miriam, and Tatiana M. Gelfeld. "Estimating Mental Workload through Event-Related Fluctuations of Pupil Area during a Task in a Virtual World." Applied Neuroscience: Functional Enhancement, Prevention, Characterisation and Methodology. (Hosting the Society of Applied Neuroscience) 93, No. 1 (Jul. 1, 2014): 38-44. https://doi.org/10.1016/j.jpsycho.2013.11.002.

S. P. Marshall. "The Index of Cognitive Activity: Measuring Cognitive Workload." In Proceedings of the IEEE 7th Conference on Human Factors and Power Plants, 7-7, 2002. https://doi.org/10.1109/HFPP.2002.1042860.

Schlag, J., M. Schlag-Rey, and I. Pigarev. "Supplementary Eye Field: Influence of Eye Position on Neural Signals of Fixation." Experimental Brain Research 90, No. 2 (Aug. 1, 1992): 302-6. https://doi.org/10.1007/BF00227242.

Stuss, Donald T., Michael P. Alexander, Carole L. Palumbo, Leslie Buckle, Lisa Sayer, and Janice Pogue. "Organizational Strategies with Unilateral or Bilateral Frontal Lobe Injury in Word Learning Tasks." Neuropsychology 8, No. 3 (1994): 355-73. https://doi.org/10.1037/0894-4105.8.3.355.

Swick, Diane, and Robert T. Knight. "Is Prefrontal Cortex Involved in Cued Recall? A Neuropsychological Test of PET Findings." Neuropsychologia 34, No. 10 (Oct. 1, 1996): 1019-28. https://doi.org/10.1016/0028-3932(96)00011-5.

Yerkes, Robert M., and John D. Dodson. "The Relation of Strength of Stimulus to Rapidity of Habit-Formation." Journal of Comparative Neurology and Psychology 18, No. 5 (Nov. 1, 1908): 459-82. https://doi.org/10.1002/cne.920180503.

Kardon, R. H., Corbett, J. J., & Thompson, H. S. (1997). Segmental denervation and reinnervation of the iris sphincter as shown by infrared videographic transillumination. Ophthalmology, 105(2), 313-321.

\* cited by examiner

OCULAR SYSTEM TO OPTIMIZE LEARNING

CROSS-REFERENCE TO RELATED APPLICATIONS

This non-provisional patent application claims priority to provisional application 62/950,918 filed on Dec. 19, 2019, the entire contents of which are fully incorporated herein with these references.

DESCRIPTION

Field of the Invention

The present invention generally relates to ocular systems. More particularly, the present invention relates to ocular systems where one can perform deception detection, assessment of operational risk and optimized learning, which may be enabled by transillumination of the iris muscles to infer stroma deformation.

Background of the Invention

The inventors of this present application have substantial experience in ocular system disclosed by provisional patent application 62/239,840; U.S. Pat. No. 10,575,728 issued on Mar. 3, 2020; and patent application Ser. No. 16/783,128 filed on Feb. 5, 2020 which is now U.S. Publication 2020/0170560—the entire contents of which are fully incorporated herein with these references Accordingly, there is a need for improved ocular systems. The present invention fulfills these needs and provides other related advantages.

SUMMARY OF THE INVENTION

Ocular System for Deception Detection

An exemplary embodiment of the present invention is a method of deception detection based upon ocular information of a subject, the method comprising the steps of: providing a standoff device configured to view the subject during an examination, the standoff device not in physical contact with the subject, wherein the standoff device has at least one video camera configured to record a close-up view of at least one eye of the subject, and wherein the standoff device has or is connected to a computing device; providing a cognitive state model configured to determine a high to a low cognitive load experienced by the subject, the cognitive load measuring the extent to which the subject is drawing on mental resources to formulate their response; providing an emotional state model configured to determine a high to a low state of arousal experienced by the subject, the state of arousal based upon the subject's nervous system activation; recording, via the at least one video camera, the ocular information of the at least one eye of the subject; establishing a baseline state of the ocular information of the at least one eye of the subject before questioning of the subject; asking a question of the subject and allowing the subject to answer the question; after asking the question and including the time of the subject answering the question, processing the ocular information to identify changes in ocular signals of the subject; evaluating, via the computing device, the cognitive state model and the emotional state model based solely on the changes in ocular signals and estimating a probability of the subject being either truthful or deceptive; determining a binary output of either truthfulness or deceptiveness; and displaying the binary output to an administrator.

In other exemplary embodiments the changes in ocular signals may comprise any of the following: eye movement, gaze location X, gaze location Y, saccade rate, saccade peak velocity, saccade average velocity, saccade amplitude, fixation duration, fixation entropy (spatial), gaze deviation (polar angle), gaze deviation (eccentricity), re-fixation, smooth pursuit, smooth pursuit duration, smooth pursuit average velocity, smooth pursuit amplitude, scan path (gaze trajectory over time), pupil diameter, pupil area, pupil symmetry, velocity (change in pupil diameter), acceleration (change in velocity), jerk (pupil change acceleration), pupillary fluctuation trace, constriction latency, dilation duration, spectral features, iris muscle features, iris muscle group identification, iris muscle fiber contractions, iris sphincter identification, iris dilator identification, iris sphincter symmetry, pupil and iris centration vectors, blink rate, blink duration, blink latency, blink velocity, partial blinks, blink entropy (deviation from periodicity), sclera segmentation, iris segmentation, pupil segmentation, stroma change detection, eyeball area (squinting), deformations of the stroma, iris muscle changes.

In other exemplary embodiments the step of estimating the probability of the subject being either truthful or deceptive comprises a plurality of estimates taken over a period of time during the subject's answer, wherein the plurality of estimates are weighted and combined to produce the binary output.

In other exemplary embodiments the at least one video camera may capture frames at a rate of at least 100 frames per second, 50 frames per second or 30 frames per second.

In other exemplary embodiments the standoff device may include a second video camera configured to record the entirety of the subject's face.

In other exemplary embodiments the computing device may be a cloud-based computing device disposed remote from the standoff device.

In other exemplary embodiments the computing device may be part of the standoff device or may be separate from the standoff device.

In other exemplary embodiments, after asking the question of the subject and allowing the subject to answer the question, one may wait a period of time and re-establishing the baseline state of the ocular information of the at least one eye of the subject before an additional question is asked of the subject.

In other exemplary embodiments an entire statement by the subject may be evaluated as the answer to question.

In other exemplary embodiments the step of saving each binary output and each corresponding video recorded by the at least one video camera may be by the computing device.

Ocular System to Assess Operational Risk

An exemplary embodiment of the present invention 1. A method of assessing operational risk based upon ocular information of a subject, the method comprising the steps of: providing a video camera configured to record a close-up view of at least one eye of the subject; providing an electronic display screen configured to display a plurality of images to the subject; providing a computing device electronically connected to the video camera and the electronic display; displaying, via the electronic display, at least one oculomotor task; recording, via the video camera, the ocular information of the at least one eye of the subject during the at least one oculomotor task; processing, via the computing device, the ocular information to identify changes in ocular signals of the subject through the use of convolutional neural networks; evaluating, via the computing device, the changes in ocular signals from the convolutional neural networks combined with the at least one oculomotor task corresponding to the changes in ocular signals by a machine learning algorithm; determining, via the machine learning algorithm, a duty fitness result for the subject; wherein the duty fitness result is either fit for duty, unfit for duty or more information needed; and displaying, to the subject and/or to a supervisor, the duty fitness result for the subject.

In other exemplary embodiments the changes in ocular signals may comprise any of the following: eye movement, gaze location X, gaze location Y, saccade rate, saccade peak velocity, saccade average velocity, saccade amplitude, fixation duration, fixation entropy (spatial), gaze deviation (polar angle), gaze deviation (eccentricity), re-fixation, smooth pursuit, smooth pursuit duration, smooth pursuit average velocity, smooth pursuit amplitude, scan path (gaze trajectory over time), pupil diameter, pupil area, pupil symmetry, velocity (change in pupil diameter), acceleration (change in velocity), jerk (pupil change acceleration), pupillary fluctuation trace, constriction latency, dilation duration, spectral features, iris muscle features, iris muscle group identification, iris muscle fiber contractions, iris sphincter identification, iris dilator identification, iris sphincter symmetry, pupil and iris centration vectors, blink rate, blink duration, blink latency, blink velocity, partial blinks, blink entropy (deviation from periodicity), sclera segmentation, iris segmentation, pupil segmentation, stroma change detection, eyeball area (squinting), deformations of the stroma, iris muscle changes.

In other exemplary embodiments the at least one oculomotor task may comprise any of the following: pupillary light reflex, optokinetic reflex, horizontal gaze nystagmus, smooth pursuit, gaze calibration or startle response.

In other exemplary embodiments the electronic display screen may be that of a smart phone, a tablet, a laptop screen, a desktop screen or an electronic screen.

In other exemplary embodiments the video camera, the electronic display screen and the computing device may all contained as a smart phone or as a tablet.

An exemplary embodiment of the present invention is a method of assessing operational risk based upon ocular information of a subject, the method comprising the steps of: providing a video camera configured to passively record a close-up view of at least one eye of the subject; providing a computing device electronically connected to the video camera and the electronic display; recording, via the video camera, the ocular information of the at least one eye of the subject; processing, via the computing device, the ocular information to identify changes in ocular signals of the subject through the use of convolutional neural networks; evaluating, via the computing device, the changes in ocular signals from the convolutional neural networks by a machine learning algorithm; determining, via the machine learning algorithm, a duty fitness result for the subject; wherein the duty fitness result is either fit for duty, unfit for duty or more information needed; and displaying, to the subject and/or to a supervisor, the duty fitness result for the subject.

In other exemplary embodiments the changes in ocular signals may comprise any of the following: eye movement, gaze location X, gaze location Y, saccade rate, saccade peak velocity, saccade average velocity, saccade amplitude, fixation duration, fixation entropy (spatial), gaze deviation (polar angle), gaze deviation (eccentricity), re-fixation, smooth pursuit, smooth pursuit duration, smooth pursuit average velocity, smooth pursuit amplitude, scan path (gaze trajectory over time), pupil diameter, pupil area, pupil symmetry, velocity (change in pupil diameter), acceleration (change in velocity), jerk (pupil change acceleration), pupillary fluctuation trace, constriction latency, dilation duration, spectral features, iris muscle features, iris muscle group identification, iris muscle fiber contractions, iris sphincter identification, iris dilator identification, iris sphincter symmetry, pupil and iris centration vectors, blink rate, blink duration, blink latency, blink velocity, partial blinks, blink entropy (deviation from periodicity), sclera segmentation, iris segmentation, pupil segmentation, stroma change detection, eyeball area (squinting), deformations of the stroma, iris muscle changes.

In other exemplary embodiments the duty fitness result may relate to a level of intoxication of the subject.

In other exemplary embodiments the duty fitness result may relate to a level of impairment of the subject.

In other exemplary embodiments the duty fitness result may relate to a level of fatigue of the subject.

In other exemplary embodiments the duty fitness result may relate to a level of anxiety and/or stress of the subject.

Ocular System to Optimize Learning

An exemplary embodiment of the present invention is a method to optimize learning based upon ocular information of a subject, the method comprising the steps of: providing a video camera configured to record a close-up view of at least one eye of the subject; providing a first electronic display configured to display a plurality of educational subject matter to the subject; providing a second electronic display configured to display an output to an instructor; providing a computing device electronically connected to the video camera, the first electronic display and the second electronic display; recording, via the video camera, the ocular information of the at least one eye of the subject while learning the plurality of educational subject matter; processing, via the computing device, the ocular information to identify changes in ocular signals of the subject through the use optimized algorithms; providing a cognitive state model configured to determine a low to a high cognitive load experienced by the subject, the cognitive load measuring the extent to which the subject is drawing on mental resources; evaluating, via the computing device, the cognitive state model based on the changes in the ocular signals and determining a probability of the low to the high cognitive load experienced by the subject; and displaying, via the second electronic display, the probability of the low to the high cognitive load experienced by the subject to the instructor.

In other exemplary embodiments it may include the steps of, via the computing device, establishing a location of the first electronic display in relation to the at least one eye of the subject; determining from the changes in ocular signals a subject's gazing location in relation to the plurality of educational subject matter; linking the subject's gaze location of the plurality of the educational subject matter and the changes in ocular signals to the subject's cognitive load; and displaying, via the second electronic display to the instructor, the subject's cognitive load in relation to the plurality of educational subject matter.

In other exemplary embodiments it may include the step of isolating a pupil dilation of the subject resulting from changes in cognitive load from changes in ambient luminance by utilizing a power spectral density frequency transformation.

In other exemplary embodiments it may include the steps of providing an optimal learning scale model having a learning scale for the subject based upon a representative population or a subject's prior data, the learning scale ranging from under stimulated to overwhelmed; evaluating, via the computing device, the changes in ocular signals to determine the subject's position along the learning scale; and displaying, via the second display to the instructor, the subject's position along the learning scale.

In other exemplary embodiments it may include the steps of providing a memory formation model configured to determine a strength of short-term and/or long-term memories; evaluating, via the computing the device, the changes in ocular signals to determine the subject's strength of the short-term and/or the long-term memories in relation to the plurality of educational subject matter; and displaying, via the second display to the instructor, the subject's strength of the short-term and/or the long-term memories in relation to the plurality of educational subject matter.

In other exemplary embodiments the changes in ocular signals may comprise any of the following: eye movement, gaze location X, gaze location Y, saccade rate, saccade peak velocity, saccade average velocity, saccade amplitude, fixation duration, fixation entropy (spatial), gaze deviation (polar angle), gaze deviation (eccentricity), re-fixation, smooth pursuit, smooth pursuit duration, smooth pursuit average velocity, smooth pursuit amplitude, scan path (gaze trajectory over time), pupil diameter, pupil area, pupil symmetry, velocity (change in pupil diameter), acceleration (change in velocity), jerk (pupil change acceleration), pupillary fluctuation trace, constriction latency, dilation duration, spectral features, iris muscle features, iris muscle group identification, iris muscle fiber contractions, iris sphincter identification, iris dilator identification, iris sphincter symmetry, pupil and iris centration vectors, blink rate, blink duration, blink latency, blink velocity, partial blinks, blink entropy (deviation from periodicity), sclera segmentation, iris segmentation, pupil segmentation, stroma change detection, eyeball area (squinting), deformations of the stroma, iris muscle changes.

In other exemplary embodiments the step of recording, via the video camera, the ocular information of the at least one eye of the subject while learning the plurality of educational subject matter may also include recording, via the camera, a facial expression and/or a posture of the subject while learning the plurality of educational subject matter.

An exemplary embodiment of the present invention is a method to measure a cognitive load based upon ocular information of a subject, the method comprising the steps of: providing a video camera configured to record a close-up view of at least one eye of the subject; providing a computing device electronically connected to the video camera and the electronic display; recording, via the video camera, the ocular information of the at least one eye of the subject; processing, via the computing device, the ocular information to identify changes in ocular signals of the subject through the use of convolutional neural networks; evaluating, via the computing device, the changes in ocular signals from the convolutional neural networks by a machine learning algorithm; determining, via the machine learning algorithm, the cognitive load for the subject; and displaying, to the subject and/or to a supervisor, the cognitive load for the subject.

In other exemplary embodiments the changes in ocular signals may comprise any of the following: eye movement, gaze location X, gaze location Y, saccade rate, saccade peak velocity, saccade average velocity, saccade amplitude, fixation duration, fixation entropy (spatial), gaze deviation (polar angle), gaze deviation (eccentricity), re-fixation, smooth pursuit, smooth pursuit duration, smooth pursuit average velocity, smooth pursuit amplitude, scan path (gaze trajectory over time), pupil diameter, pupil area, pupil symmetry, velocity (change in pupil diameter), acceleration (change in velocity), jerk (pupil change acceleration), pupillary fluctuation trace, constriction latency, dilation duration, spectral features, iris muscle features, iris muscle group identification, iris muscle fiber contractions, iris sphincter identification, iris dilator identification, iris sphincter symmetry, pupil and iris centration vectors, blink rate, blink duration, blink latency, blink velocity, partial blinks, blink entropy (deviation from periodicity), sclera segmentation, iris segmentation, pupil segmentation, stroma change detection, eyeball area (squinting), deformations of the stroma, iris muscle changes.

Transillumination of Iris Muscles to Infer Stroma Deformation

An exemplary embodiment of the present invention is a method of discovering relationships between iris physiology and cognitive states and/or emotional states of a subject, the method comprising the steps of: providing a computing device; providing a video camera configured to record a close-up view of at least one eye of the subject; providing a first light configured to be held to a skin of a lower eyelid of the subject allowing light to shine out from within the at least one eye; providing a second light configured to not be in contact with the subject located a distance apart from the subject and configured to illuminate a stroma of the at least one eye of the subject; wherein the first light and the second light are electronically synced together and configured to flash alternatively; engaging the user in a plurality of tasks, each task of the plurality of tasks configured to be cognitively or emotionally evocative; recording, via the video camera, ocular information comprising responses in the iris musculature and corresponding distortions in the stroma due to the cognitive state and/or the emotional state of the subject produced by the plurality of tasks; processing, via the computing device, the ocular information to identify correlations between the responses in the iris musculature and the distortions in the stroma through the use optimized algorithms; and identifying, via the computing device, at least one predictive distortion in the stroma capturable solely with a visible-spectrum camera correlating to a predicted responses in the iris musculature when the subject was in the cognitive state and/or the emotional state produced by the plurality of tasks.

In other exemplary embodiments the first light may comprise a (150 mw) NIR LED. The second light may comprise a (150 mw) NIR LED.

In other exemplary embodiments the first light and the second light may be configured to flash alternatively (at 160 Hz) producing a resultant effect (of 80 Hz).

In another exemplary embodiment, it could further include a method of generating near infrared images from visible light images, the method comprising the steps of: providing a visible spectrum video camera configured to record the close-up view of the at least one eye of the subject; recording, via the visible spectrum video camera, the ocular information comprising the distortions in the stroma due to the cognitive state and/or the emotional state of the subject; predicting, via the computing device, an infrared image of the at least one eye of the subject through a generative adversarial network using the ocular information from the visible spectrum video camera; wherein the predicting, via the computing device, utilizes the at least one predictive distortion in the stroma for creating the infrared image.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
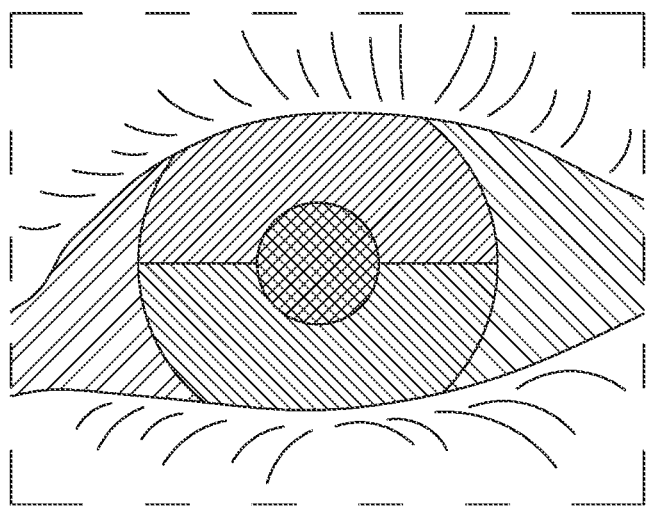
FIG. 1 is a front view of an eye of the subject showing a masking technique based on a UNET neural network.

It is noted herein that the reference to "Senseye" in the present application is a reference to the company (i.e. the Applicant) of the inventors.

Ocular System for Deception Detection:

The Senseye Deception Detector is a standoff device designed to use ocular signals to detect deception in a variety of settings, including structured questions, active interrogation, and passively viewing a human. The device records ocular signals and classifies a person's statement as truthful or deceptive. It provides a binary classification. The classification of each question is based solely on the ocular information obtained at the time of the response or statement, and therefore the system design allows for classification of each question individually with no duplicate questions or specific question structure necessary. This is an advance over many systems and techniques for detecting deception, which rely on multiple instances of a question topic to arrive at a conclusion, or rely on comparing the results of questions to each other. The thresholds for deception can be set based on the use case (e.g., more stringent parameters for higher stakes situations).

The Deception Detector uses a combination of models of cognitive and emotional states to feed into the final deception model and classification. As such, the system is capable of outputting a binary classification of the results of the component models. It outputs a classification of high or low cognitive load, which measures the extent to which the person is drawing on mental resources to formulate their response. It outputs a classification of high or low arousal, which is based on the subject's nervous system activation. Both of these measures are intended to provide context for the classification of deception.

It is also understood by those skilled in the art that the Senseye Deception Detector could be reconfigured to not be a standoff device and instead reside, at least partially, in a head gear, hat, pair of glasses and the like that would be worn or held by the user. This manner of monitoring and viewing the subject would be more intrusive, but would still use the rest of the methods and strategies as taught herein.

The Deception Detector relies on ocular signals to make its classification. These changes in ocular signals may comprise any of the following: eye movement, gaze location X, gaze location Y, saccade rate, saccade peak velocity, saccade average velocity, saccade amplitude, fixation duration, fixation entropy (spatial), gaze deviation (polar angle), gaze deviation (eccentricity), re-fixation, smooth pursuit, smooth pursuit duration, smooth pursuit average velocity, smooth pursuit amplitude, scan path (gaze trajectory over time), pupil diameter, pupil area, pupil symmetry, velocity (change in pupil diameter), acceleration (change in velocity), jerk (pupil change acceleration), pupillary fluctuation trace, constriction latency, dilation duration, spectral features, iris muscle features, iris muscle group identification, iris muscle fiber contractions, iris sphincter identification, iris dilator identification, iris sphincter symmetry, pupil and iris centration vectors, blink rate, blink duration, blink latency, blink velocity, partial blinks, blink entropy (deviation from periodicity), sclera segmentation, iris segmentation, pupil segmentation, stroma change detection, eyeball area (squinting), deformations of the stroma, iris muscle changes.

The signals are acquired using a multistep process designed to extract nuanced information from the eye. As shown in FIG. 1, image frames from video data are processed through a series of optimized algorithms designed to isolate and quantify structures of interest. These isolated data are further processed using a mixture of automatically optimized, hand parameterized, and non-parametric transformations and algorithms. Leveraging the time series character of these signals and the cognitive load and arousal contextual information, some of these methods specifically estimate the probability of the input data representing a deceptive state. Multiple estimates are combined and weighted to produce a model that classifies a response or statement, based on the ocular signals that occur during such, as truthful or deceptive.

Figure 2A:
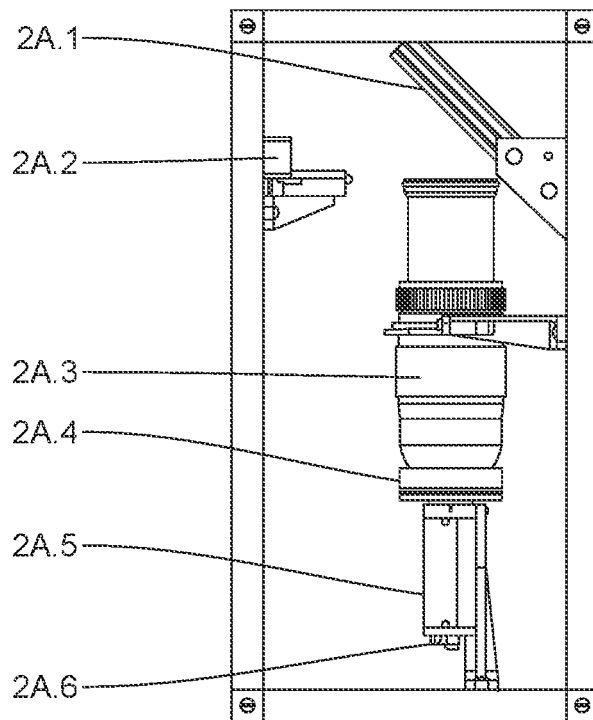
FIG. 2A illustrates a side view of a camera system of the present invention.

The product functions by processing the ocular metrics resulting from our computer vision segmentation and analyzing these outputs during time-linked events occurring in the world. One version of the Deception Detector functions on a specific Senseye hardware design. This embodiment of the device (see FIG. 2A) has a box with an opening designed to sit at eye level standoff from the participant. A video camera, such as a webcam, is facing the participant captures their head, parsing the eye using facial keypoints. Once the eye location is determined, the high resolution camera automatically adjusts to get a close up view of the left eye (or right eye). As shown in the embodiment of FIG. 2A there is a mirror 2A.1, a USB webcam 2A.2, Canon 70-300 USM AF lens 2A.3, C-Mount to Canon EF Adapter 2A.4, Emergent HR-12000-S-M 2A.5 and 10 GigE SFP+ 2A.6.

The camera allows for extremely high fidelity iris segmentation. A high connection speed allows for over 100 frames per second of update speed, making even the subtlest and quickest changes in eye physiology detectable. However, slower frame rates can be used such as frame rates of 50 or 30 frame per second. An adapter mount allows for focal lengths that can fill the frame with an eye from over a meter away. In addition, the adapter allows the Senseye system to control the focus ring and aperture via software. Video data is stored in raw format, and processed tabular data is stored in a local database.

Figure 2B:
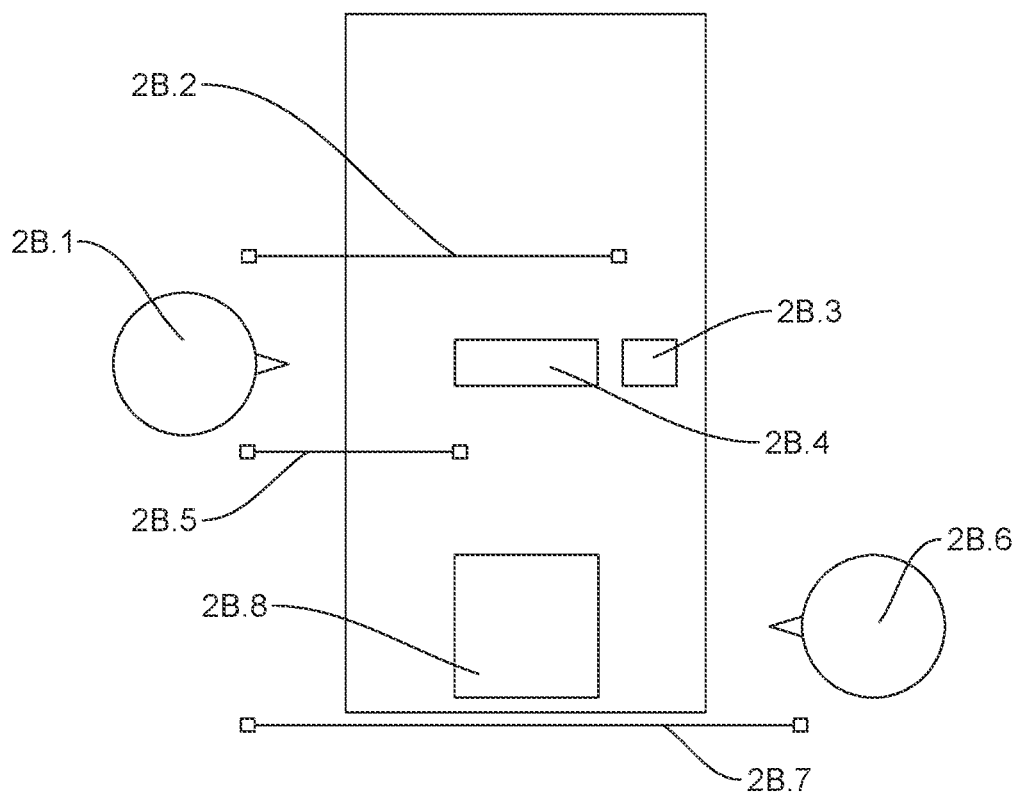
FIG. 2B illustrates a schematic top view of a subject utilizing the present invention.

One possible use case illustrating the placement and distances of the user, subject and system is also shown in FIG. 2B. The camera is placed perpendicular to the user and a 45 degree angle mirror is used to capture the eye. The user can choose to autofocus the lens on a per-session basis. The system alleviates the need for manual focus and removes a point of human error. As shown in the embodiment of FIG. 2B, the subject 2B.1 is a distance 2B.2 of 36 inches from the fixation point 2B.3. The camera 2B.4 is a distance 2B.5 of 24 inches. As shown here the experimenter 2B.6 is a distance 2B.7 of about 52 inches. Also on the table is the device 2B.8 of the present invention.

This hardware setup is one of several ways the system is designed to work. The system can also offload its computational workload to an external solution such as a cloud instance or an on-site compute node.

Figure 3:
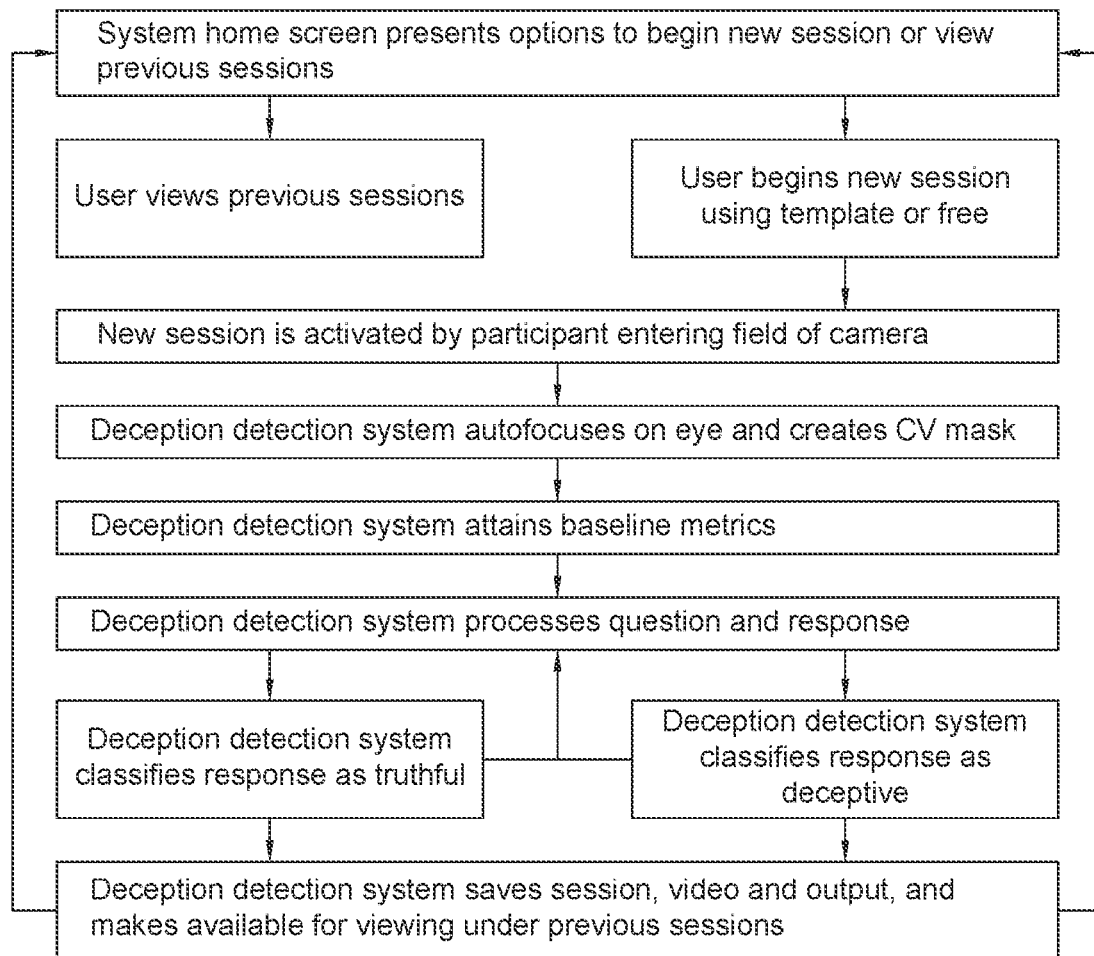
FIG. 3 is a flow chart of one embodiment of the present invention.

In both cases the system functions following the outline in FIG. 3. At the beginning of an assessment the system records metrics which generate a baseline reading of the subject. Many of the metrics listed above and included in the model are based on different kinds of change from these baseline readings. These changes act as inputs into the model and allow for an immediate classification of the response as truthful or deceptive. In between each question, time is allowed for the interviewee's nervous system and ocular metrics to return to baseline. After this reset period, typically 10 seconds, the interviewer proceeds to the next question and again receives a classification of deception or truth immediately after the response.

In addition to the immediate classifications, the system outputs an after session report displaying the results given for each question. It offers the option to download the data file containing the readings for each metric in the model timestamped to the events occuring over the entire session. It has the option to go back and view the video and classification results of any previously recorded session. The system has other features which make it flexible for different use cases. It provides the option to create a template of questions, which can be ordered and automated for repeated screenings. It can be operated with no template as well, for free questioning. Finally, it can run off of videos in which a participant is making statements with no questions asked. In this case, the entire video statement is viewed as one question by the system, and a classification is output in the same fashion, with the same after action options, once the video is complete.

Ocular System to Assess Operational Risk:

The Senseye Operational Risk Management (ORM) System provides an objective measure of a worker's fitness to work. The system screens the worker for excessive fatigue, alcohol or drug impairment, and psychological risk factors that could interfere with job performance and safety. The system records video of the user's eyes while they perform various oculomotor tasks and/or passively view a screen. The ORM system also includes the software that presents the stimuli to the user. The system uses computer vision to segment the eyes and quantify a variety of ocular features. The ocular metrics then become inputs to a machine learning algorithm designed to detect when workers are too fatigued or impaired (due to drugs, alcohol, or psychological risk factors) to safely perform their job. The thresholds for fitness can be set based on the use case (e.g., more stringent parameters for high stakes/high risk occupations). A further application of the ORM models and thresholds is that they can be implemented on video that passively watches a user as they are performing a task, with no screening stimuli needed.

The primary input to the Senseye ORM system is video footage of the eyes of the user while they perform the oculomotor tasks presented by the system or passively view the phone or tablet screen or computer monitor. The location and identity of visible anatomical features from the open eye (i.e., sclera, iris, and pupil) are classified in digital images in a pixel-wise manner via convolutional neural networks originally developed for medical image segmentation. Based on the output of the convolutional neural network, numerous ocular features are produced. These ocular metrics are combined with event data from the oculomotor tasks which provide context and labels. The ocular metrics and event data are provided to the machine learning algorithms which then return a result of "fit for duty", "unfit for duty", or "more information needed." The system will also return the reason behind an "unfit for duty" designation (e.g., excessive fatigue, suspected drug or alcohol impairment, excessive anxiety).

ORM relies on ocular signals to make its classifications. These changes in ocular signals may comprise any of the following: eye movement, gaze location X, gaze location Y, saccade rate, saccade peak velocity, saccade average velocity, saccade amplitude, fixation duration, fixation entropy (spatial), gaze deviation (polar angle), gaze deviation (eccentricity), re-fixation, smooth pursuit, smooth pursuit duration, smooth pursuit average velocity, smooth pursuit amplitude, scan path (gaze trajectory over time), pupil diameter, pupil area, pupil symmetry, velocity (change in pupil diameter), acceleration (change in velocity), jerk (pupil change acceleration), pupillary fluctuation trace, constriction latency, dilation duration, spectral features, iris muscle features, iris muscle group identification, iris muscle fiber contractions, iris sphincter identification, iris dilator identification, iris sphincter symmetry, pupil and iris centration vectors, blink rate, blink duration, blink latency, blink velocity, partial blinks, blink entropy (deviation from periodicity), sclera segmentation, iris segmentation, pupil segmentation, stroma change detection, eyeball area (squinting), deformations of the stroma, iris muscle changes.

The Senseye ORM system is designed to run on a variety of hardware options. The eye video can be acquired by a webcam, cell phone camera, or any other video camera with sufficient resolution and frame rate. The stimuli can be presented on a cell phone, tablet, or laptop screen or a standard computer monitor. The necessary hardware to run the software is neural-network-capable fpgas, asics or accelerated hardware; either within the device or on a server accessed through an API.

The Senseye ORM assessment begins with the user initiating the process by logging in to the system. This can be achieved by typing a username and password, or using facial recognition. In one embodiment, the user is presented with a series of oculomotor tasks which may include the pupillary light reflex, optokinetic reflex, nystagmus test, and smooth pursuit. A gaze calibration task may also be included to improve the gaze measurements output by the system. Each task is described briefly below. Depending on the use case, a subset of these tasks will be included. In another embodiment, the scan is designed to be more passive, so the user's eyes are recorded while they passively view a screen.

Figure 4:
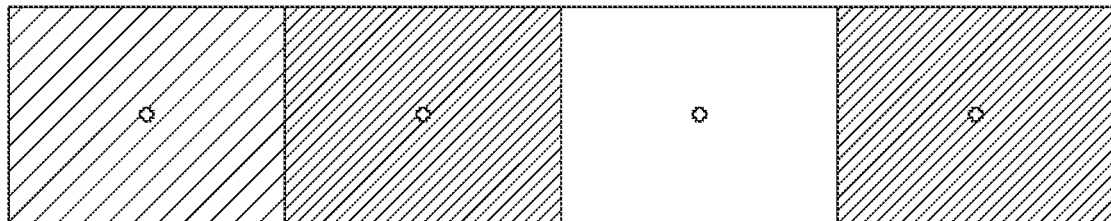
FIG. 4 illustrates an example of pupillary light reflex test of the present invention.

FIG. 4 illustrates an example of pupillary light reflex. The pupillary light reflex is measured by the ORM system by manipulating the luminance of the screen. The user fixates a cross in the center of the screen while the screen changes from grey to black to white then back to black. The bright white screen causes the pupil to constrict. The pupil size is measured using computer vision and various parameters such as constriction latency, velocity and amplitude are computed. Atypical pupil dynamics can be indicative of fatigue, intoxication, stress/anxiety, and the sympathetic hyperactivity indicative of PTSD.

Figure 5:
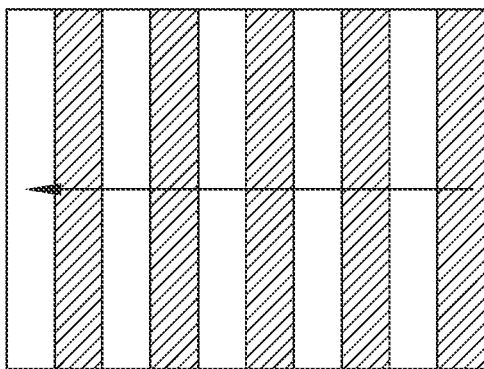
FIG. 5 illustrates an example of optokinetic reflex of the present invention.

FIG. 5 illustrates an example of optokinetic reflex. The optokinetic reflex is induced by presenting the user with alternating black and white bars moving across the screen. The eye will reflexively track a bar moving across the screen and then move back to the starting point once the bar has moved off the screen. This produces a characteristic sawtooth pattern in the gaze x position of the eye, which should correspond to the stimulus velocity. Deviations from the stimulus velocity indicated that the optokinetic reflex is impaired.

Figure 6:
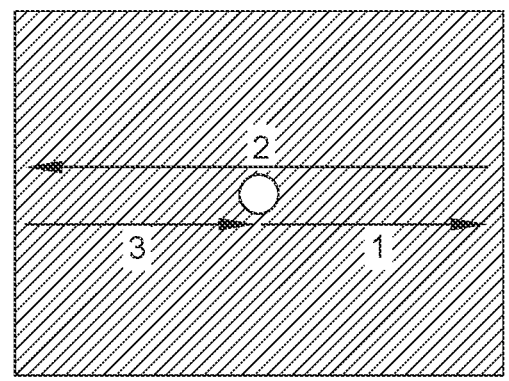
FIG. 6 illustrates an example of horizontal gaze nystagmus of the present invention.

FIG. 6 illustrates an example of horizontal gaze nystagmus. The nystagmus test is similar to a component of the field sobriety test used by law enforcement. A circular stimulus moves horizontally across the screen, traversing 45 degrees of visual angle in each direction. The user is instructed to track the stimulus with their eyes. In a healthy individual, involuntary horizontal eye oscillations are expected to occur once the eyes have moved 40-45 degrees to the right or left. If a user is intoxicated this involuntary movement will occur at a smaller visual angle.

Figure 7:
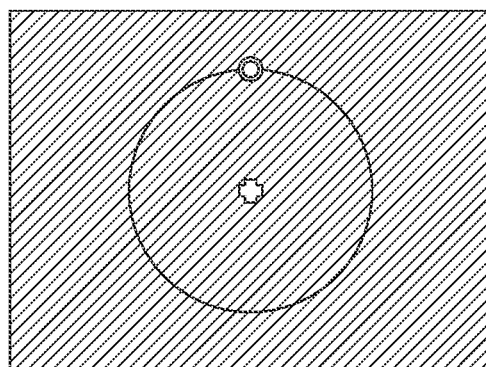
FIG. 7 illustrates an example of smooth pursuit of the present invention.

FIG. 7 illustrates an example of smooth pursuit. This task requires the user to track a circular stimulus moving at a constant speed with their eyes. Their ability to track the stimulus accurately in terms of speed and spatial precision is quantified. Poor matching of speed or spatial location are indicative of impairment.

Figure 8:
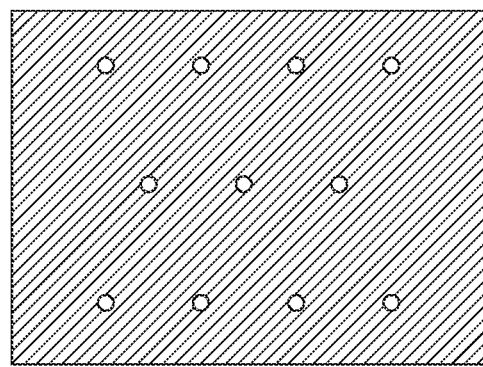
FIG. 8 illustrates an example of gaze calibration of the present invention.

FIG. 8 illustrates an example of gaze calibration. The gaze calibration task consists of a series of dots displayed in 11 different spatial locations on the screen for a few seconds each. The user is asked to fixate each dot as it appears. This task is used to calibrate the gaze tracking system to provide accurate gaze information used to assess behavior in the other tasks.

Startle response (not illustrated) is when users can be tested with loud, unpredictable bursts of white noise to test their startle response. Rapid and large dilations in response to the noise bursts are indicative of sympathetic hyperactivity.

Ongoing with development of ORM models based on the stimuli and metrics described above is their use in passive monitoring situations. In these circumstances, the product does not act as a screening device, but rather outputs classification states from the models throughout video observation of a user doing a task. These models and thresholds take advantage of the same metrics listed above, but are less dependent on context due to transfer learning from one scenario to another.

Ocular System to Optimize Learning:

The Senseye Targeted Learning System (TLS) uses non-invasive ocular measures of cognitive activity to inform and optimize the process of training and skill-based learning. TLS algorithms monitor and classify cognitive events and states, including cognitive effort, short and long-term memory usage and encoding, and alertness levels. These metrics serve individual purposes as indicators of the cognition required during a given task. Together, they are able to indicate when a person is in a state conducive to optimal learning. Over time, they are able to quantify a person's learning trajectory. Used in combination with a variety of learning curriculums, TLS aids in adapting curriculums rapidly to an individual's unique learning pace. This level of adaptive training provides accelerated learning while ensuring the retention of curriculum material. The targeted learning system includes outputs of cognitive load, a Senseye Learning Parameter (SLP) and instances of short-term and long-term memory encoding.

TLS relies on ocular signals to make its classifications. These changes in ocular signals may comprise any of the following: eye movement, gaze location X, gaze location Y, saccade rate, saccade peak velocity, saccade average velocity, saccade amplitude, fixation duration, fixation entropy (spatial), gaze deviation (polar angle), gaze deviation (eccentricity), re-fixation, smooth pursuit, smooth pursuit duration, smooth pursuit average velocity, smooth pursuit amplitude, scan path (gaze trajectory over time), pupil diameter, pupil area, pupil symmetry, velocity (change in pupil diameter), acceleration (change in velocity), jerk (pupil change acceleration), pupillary fluctuation trace, constriction latency, dilation duration, spectral features, iris muscle features, iris muscle group identification, iris muscle fiber contractions, iris sphincter identification, iris dilator identification, iris sphincter symmetry, pupil and iris centration vectors, blink rate, blink duration, blink latency, blink velocity, partial blinks, blink entropy (deviation from periodicity), sclera segmentation, iris segmentation, pupil segmentation, stroma change detection, eyeball area (squinting), deformations of the stroma, iris muscle changes.

The signals are acquired using a multistep process designed to extract nuanced information from the eye. Image frames from video data are processed through a series of optimized algorithms designed to isolate and quantify structures of interest. These isolated data are further processed using a mixture of automatically optimized, hand parameterized, and non-parametric transformations and algorithms.

Figure 9:
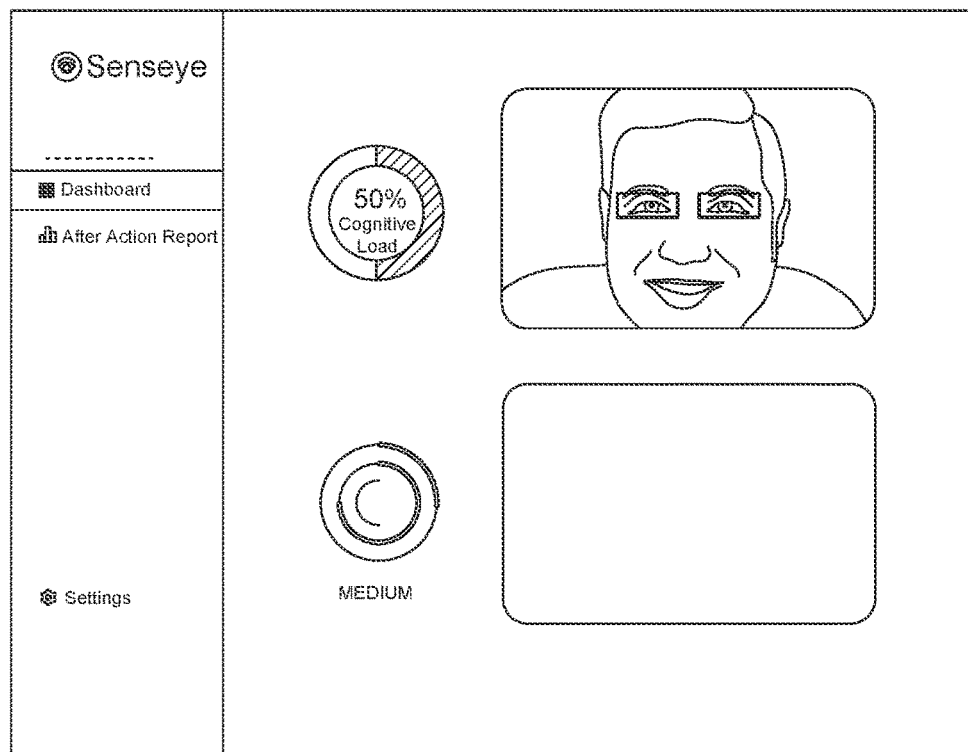
FIG. 9 shows one embodiment of the software output of the present invention.
Figure 10:
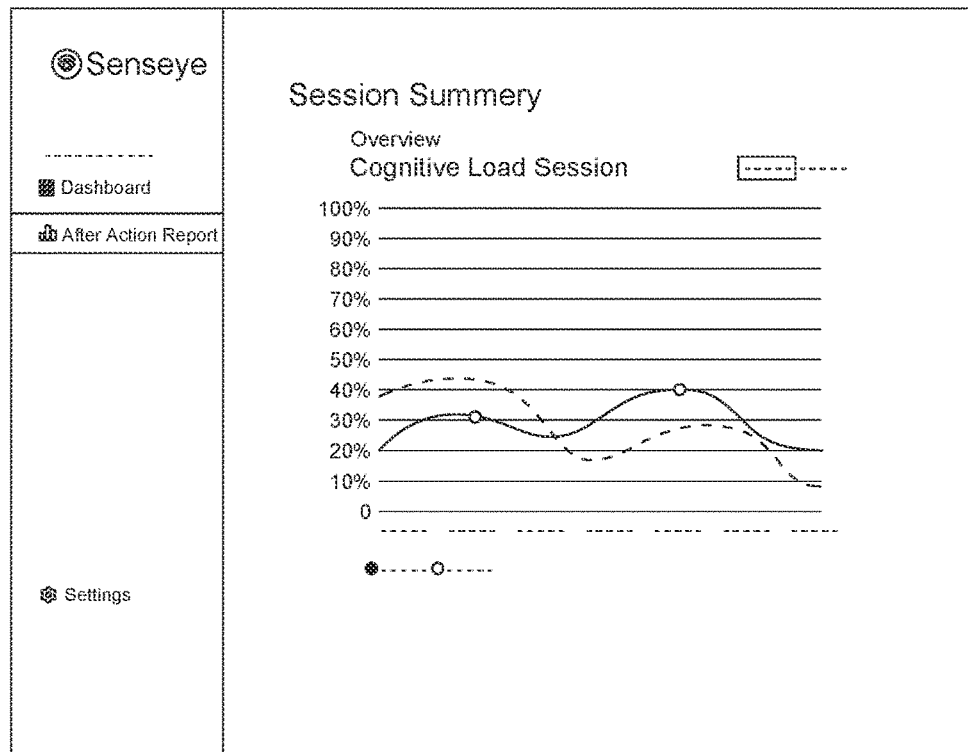
FIG. 10 shows another embodiment of the software output of the present invention.

Cognitive Load:

The TLS software is capable of working on any device with a front facing camera (tablet, phone, computer, VR headset, etc.). The TLS software uses anatomical signals (more specifically physiological signals) extracted from images to predict different cognitive states through optimized algorithms. The algorithms provide an estimated probability that the input data represents a particular cognitive state, and may identify the presence of one or more cognitive states. Image signals are run through a series of data processing operations to extract signals and estimations. Multiple image masks are first applied, isolating components of the eyes as well as facial features allowing various metrics to be extracted from the image in real-time. From the image filters, pertinent signals are extracted through transformation algorithms supporting the final estimation of cognitive states. Multiple data streams and estimations can be made in a single calculation, and cognitive load signals may stem from combinations of multiple unique processing and estimation algorithms. The cognitive load output can be directly linked to the stimulus (video and/or images and/or blank screen shown) by relating the events time and time course of the cognitive load output. The software can display, in real-time, the cognitive load of the individual as the event is occurring (FIGS. 9 and 10).

The TLS product is also capable of utilizing various forms of gaze to perform inference on cognitive states. Gaze used in this product falls into three major categories: 1) eye center estimation in frame, 2) estimation of eye position and orientation, and 3) 3D point-of-gaze estimation on the subject's focus point in space. Information cleaned from all of these approaches can be used individually or in concert. Individually, these methods offer unique and informative measurements of eye movement; together (with or without an additional calibration routine), they offer cascading informative parameters used to construct a 3D model of the eye and gaze vectors. The point of regard on an object in real space, such as a computer monitor, can then be estimated by intersecting gaze vectors with a corresponding two-dimensional plane in parallel with the surface of the object. The monitor, IR lights and nIR lights, and camera location are all known quantities before gaze estimation. Gaze of the participant is projected in the form of a heatmap onto the screen the participants are viewing. By plotting the cognitive load at the time of the gaze, the software is able to link the gaze location and the cognitive load associated with the gaze. This allows individuals to precisely analyze the location/object/task the participant was viewing when there was a change in an individual's cognitive load output.

It is unlikely that the stimulus a user is viewing will exhibit constant luminance. It is well known that perceived changes in ambient luminance are main drivers of pupillary response. To account for luminance-based pupillary response, TLS uses power spectral density (PSD) frequency transformations to isolate pupil dilation resulting from cognitive load. The PSD transformation measures the power of the waveform at each specific frequency in an interval. This method can be used to determine the various types of sinusoids that compose any kind of wave. Deconstruction of the pupillary waveform through PSD has been found to detect cognitive load regardless of luminance condition (Marshall, 2002; Nakayama & Shimizu, 2004; Hampson et al, 2010; Peysakhovich et al., 2015; Peysakhovich et al., 2017; Reiner & Gelfeld, 2014). While the luminance response is reflexive and fast, pupillary changes due to cognitive processes are slower (Joshi et al, 2016). Using a mixture of measured luminance and pupillary response signals, TLS algorithms apply PSD and other transformations, creating new and combinatory signals derived from multiple time and frequency signals. These signals then drive probability estimations of cognitive states though optimized algorithms, identifying cognitive load states even in the presence of pupillary responses from external light sources.

Figure 11:
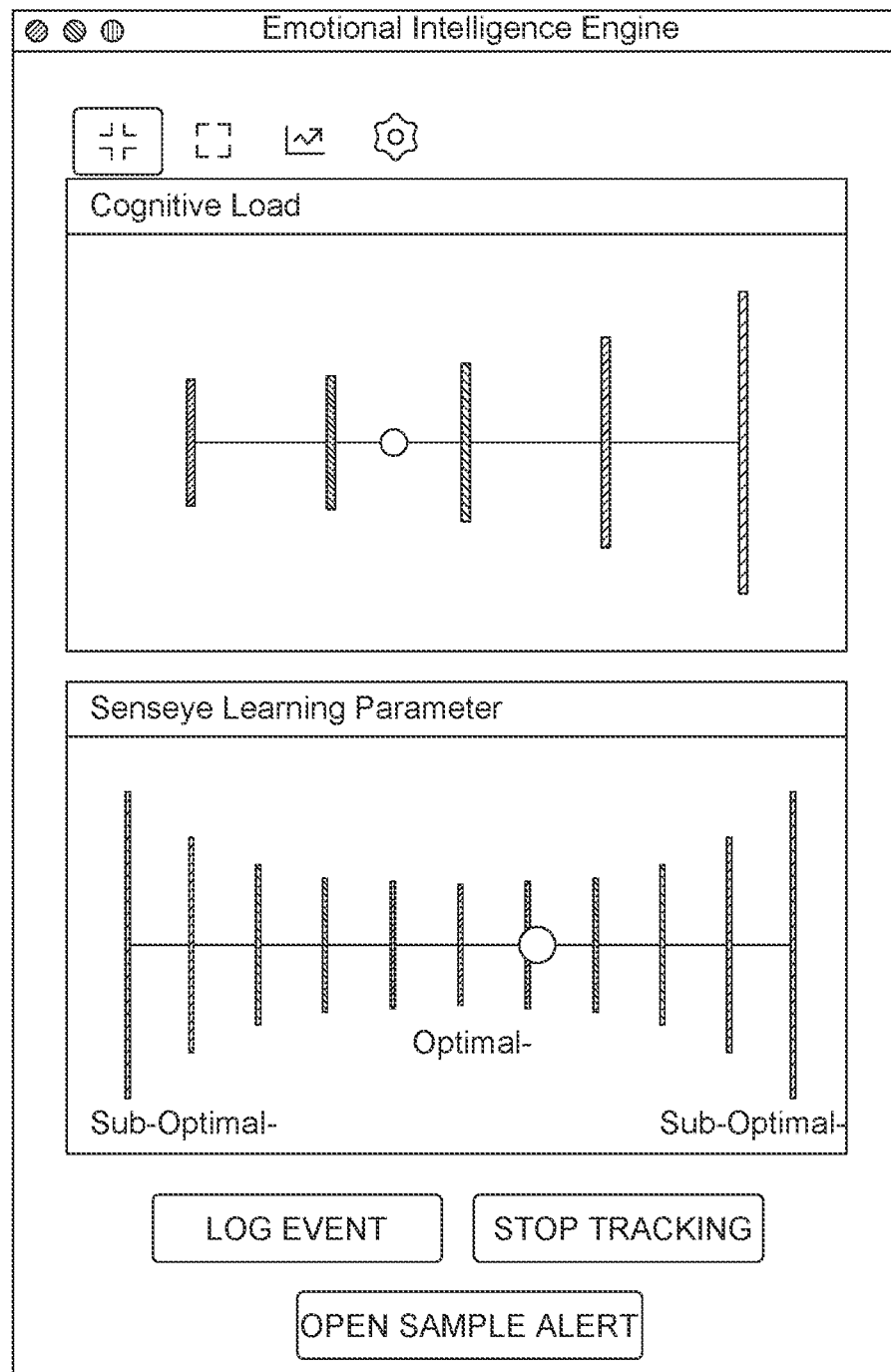
FIG. 11 is one embodiment of a cognitive load and learning parameter output of the present invention.

Senseye Learning Parameter:

As part of TLS Senseye has developed the Senseye Learning Parameter (SLP). A person's ability to learn can change depending on both internal (e.g. fatigue, low engagement, overwhelmed) and task-related (e.g. too easy, too hard) factors. SLP is part of the TLS algorithm that takes into account individuals' internal factors and is represented as a scale from low engagement/understimulated to high internal state/overwhelmed. It is computed using an algorithm which translates an individual's ocular signals into a reading on the optimal learning scale, which is statistically based either on a representative population or an individual's prior data (see Adaptive Senseye Learning Parameter). When the participant's internal state is low (sustained minimal cognitive load), the indicator shifts to the low side of the SLP scale while high internal states (sustained high cognitive load, indicating being overwhelmed) will shift the SLP indicator to the high side of the scale. This allows the instructor to adopt and adjust the task so the participant can stay in the optimal learning point (middle of the SLP) for best learning results (FIG. 11).

Adaptive Senseye Learning Parameter:

As described above, the SLP can operate on a fixed equation to generate an optimal learning parameter. However, it also has the ability to change its parameters depending on the expertise and learning ability of the subject. The amount of stress an individual can undergo while still absorbing new information varies from person to person. Under the same amount of stress and arousal, some people will maintain the ability to learn while others will not. This variation in cognitive performance at different levels of arousal has been observed in prior research (Chaby et al., 2015; Yerkes and Dodson, 1908; Anderson, 1994). The adaptive function of the SLP uses performance to determine the expertise of an individual (beginning, moderate, expert) and correlates the performance with the cognitive load to automatically generate an optimal scale for the individual. The scale is able to shift and adjust depending on changes in performance and cognitive load of the individual under conditions of stress as the individual learns and masters the task. This function further enhances the customizability of quantified learning and allows instructors or an automated lesson system to more effectively modify the curriculum to individual learning profiles.

Memory Categorization:

The TLS is also able to distinguish the occurrence and strength of memory formation including but not limited to the formation of short-term memory (STM) and long-term memory (LTM) during the learning process. Previous literature shows that different brain regions are involved in different types of memory formation. The prefrontal cortex is associated with LTM while the hippocampus is closely associated with STM. People with lesions or damage in the prefrontal cortex often have a difficult time with memory encoding and retrieval (Jetter et al., 1986; McAndrews and Milner 1991; Eslinger and Grattan 1994; Stuss and others 1994; Moscovitch and Winocur 1995) while showing little to no impairment of short-term memory (Kesner and others 1994; Stuss and others 1994; Swick and Knight 1996; Dimitrov and others 1999; Alexander and others 2003). The hippocampus is known to be involved in the formation of short-term memory and lesions in the hippocampus impair the encoding of new memories (Jonides et al., 2008; Cohen and Eichenbaum, 1993).

The prefrontal cortex is not only involved in LTM but also critical in the generation of various eye movements through transmission of motor commands to the brainstem. It is also known to modulate pupil diameter changes (Schlag-Ray et al., 1992; Ebitz and Moore, 2017) which have been associated with memory formation and retrieval (Kucewicz et al., 2018). Because both LTM and ocular metrics are associated with the prefrontal cortex, we can utilize ocular metrics to read out memory formation and build a model based on the different patterns of ocular metrics that occur during the formation of LTM and STM. Using this model, TLS has built a feature that outputs the strength and type of memory formation that occurs while a person is engaged in a learning task.

FIGS. 9 and 10 show one embodiment of TLS software output of the cognitive load session. These figures represent an iteration of the TLS user interface. FIG. 9 is a live time-series analysis of the user's cognitive load and SLP output during a specific session. In FIG. 10 there are instantaneous feeds for both cognitive load and SLP and live feeds of the eye detection and masking algorithms used to output the respective features. The eye detection algorithm locates both eyes on a user's face and focuses on one eye to segment the iris, pupil and sclera. The instantaneous readout of cognitive load is reported visually in the form of a gauge and quantitatively in the form of a percent or similar interpretation of the user's cognitive load.

FIG. 11 is one embodiment of the UI/UX of TLS cognitive load and senseye learning parameter output. One representation of cognitive load level and learning state along the SLP. The grey dot is the current state of the participant. On top is the cognitive load meter where low cognitive load is represented by green area while the high cognitive load area is presented in red. The bottom is the SLP. Similar to the cognitive load readout, the grey dot represents the current learning state of the participant. The extreme ends of the scale represent sub-optimal learning states, due to under and over stimulation.

Transillumination of Iris Muscles to Infer Stroma Deformation:

As a general overview, previous literature has shown that the iris muscles of the eye are innervated by specific regions of the brain. Activation of these brain areas results in complementary changes within respective muscle groups of the iris, and has led to the hypothesis that iris physiology can provide a non-invasive means to quantify relevant cognitive states. Notably, direct observation of iris muscle physiology is obscured by an overlying membrane known as the stroma. The technique outlined here, henceforth referred to as "transillumination", is a method for visualizing iris muscle physiology and anatomy, and subsequently visualizing how these patterns of muscle movement manifest as distortions within the overlying stroma of the iris. By mapping the association of known muscle physiology with known patterns of stroma distortion, transillumination enables the user to infer complex patterns of iris muscle physiology from simple surface level video recordings of the eye. Transillumination is an integral technology for accessing brain signals from the eye.

Senseye has developed a technique for analyzing the contributions of individual muscle groups and fibers to movements of the iris associated with cognitive and emotional states, and for mapping these movements onto the surface layer of the eye, the stroma, which is visible to off-the-shelf cameras. This innovation is a novel and sizeable step towards achieving a contact-free method of reading brain activity from ocular metrics. It involves both a conceptual innovation, and a technical innovation. The conceptual innovation is in looking at the individual movements of the muscles under different cognitive states to extract reliable signal. The technical innovation is a method by which the stroma and transilluminated muscles are visualized in such a way as to be able to be mapped onto each other.

The muscles of the iris are innervated by the parasympathetic and sympathetic nervous system. Specifically, the dilator muscles of the iris are innervated by many individual termini of the SNS, and the sphincter muscles are innervated by many individual termini of the PNS. These innervations allow information along those nervous systems' pathways to travel downstream to individual muscles of the iris, causing movements that can be measured and used to infer cognitive and emotional states. The transillumination technique of viewing and mapping the iris muscles onto the stroma allows for the creation of Senseye products that use surface level changes in the iris to model brain activity.

In regards to the process, the signal acquisition device consists of two lighting components, henceforth referred to as "lighting component one" (LC1) and "lighting component two" (LC2), and one camera. LC1 is a single 150 mw nIR LED powered by 5 volts. This is held to the skin of the lower eyelid in a manner that allows the light to shine out from within and render the musculature of the iris visible. LC2 is a 150 mw nIR standoff LED array that illuminates the exterior stroma of the iris (FIG. 1). These lighting systems are synced to flash alternatingly at 160 hz each using an oscilloscope, producing the effect of two 80 hz videos, one of the iris musculature, and one of the exterior stroma, which are perfectly in sync (FIG. 2). Video data is collected using a camera with a frame rate and resolution capable of capturing the fine movements of the iris muscles.

Figure 12:
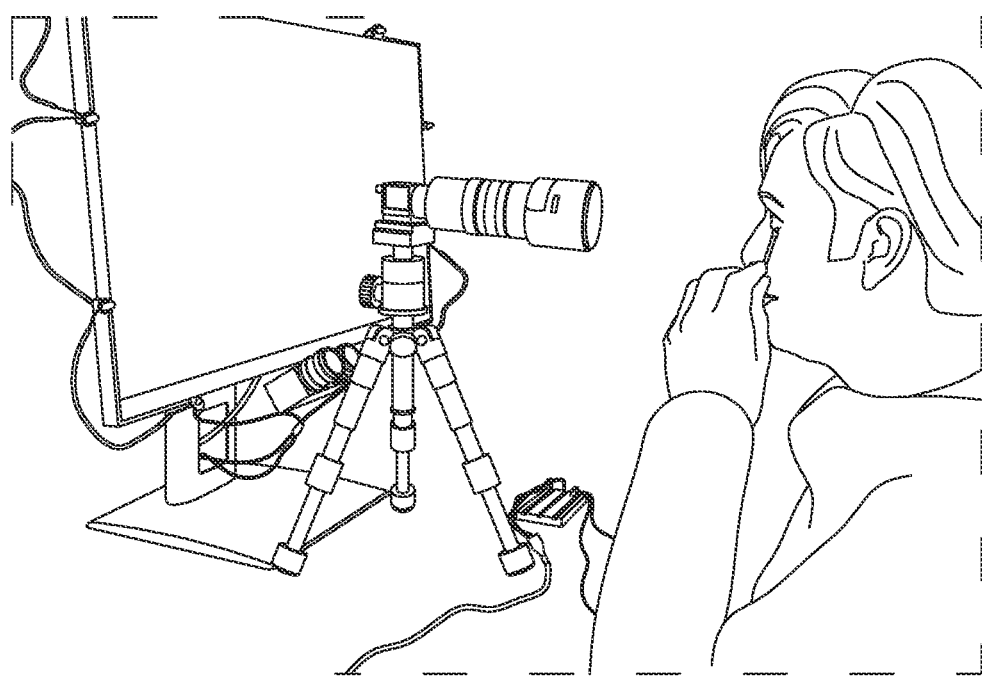
FIG. 12 shows one embodiment of the transillumination hardware and process.

The data collection protocol places the participant in a seat in front of the camera while an automated series of directions and tasks is presented (FIG. 12). The application has configurable timings for each task, changes images on the screen in front of the participant in order to induce ocular response, and provides automated instruction as to when to perform certain behaviors that are cognitively or emotionally evocative, such as arithmetic or placing one's hand in ice. The application outputs specific time stamped events in the form of tabular data to allow recorded footage to be synced with produced stimuli for proper analysis.

In the next series of analyses, image frames from video data are processed through a series of optimized algorithms and transformations designed to isolate and quantify structures of interest. Data derived from images illuminated by LC1 is used to parse structures from direct observations of iris musculature. Data derived from images illuminated by LC2 is used to parse distortions within the overlying stroma of the iris. The resulting image pairs provide unique surface-to-subsurface mapping of involuntary iris muscle actions. Extracted signals from these images are collected in a structured format and stored with pertinent experimental metadata capable of contextualizing a wide range of cognitive states and processes. These novel data sets can be used to map brain activity and surface stroma movements directly to subsurface iris activity in a measurable, reliable way.

FIG. 12 shows one embodiment of the transillumination hardware and process. One can see the participant holding an LED to eye while also illuminated by LEDs on monitor, alternating at 160 hz. The camera facing the participant capturing video of an eye.

Figure 13:
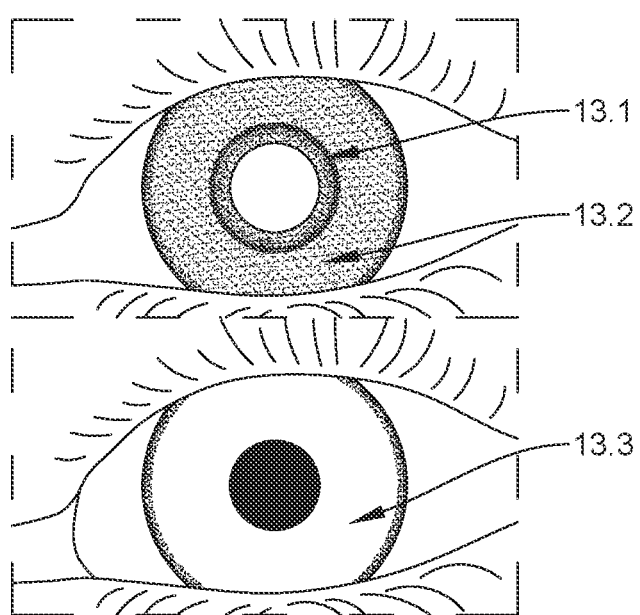
FIG. 13 is a still image of surface layer stroma and transilluminated iris video as captured with transillumination hardware of FIG. 12.

FIG. 13 is a still image of surface layer stroma and transilluminated iris video as captured with transillumination hardware. 13.1 is pointing to the transilluminated sphincter muscles, 13.2 is pointing to the transilluminated dilator muscles and 13.3 is pointing to the surface layer stroma.

Method for Generating NIR Images from RGB Cameras

The method of the present invention is using generative adversarial networks and a combination of visible and IR light which are now further discussed. Continuing the theme of creating a mapping between subsurface iris structures visible in IR light onto surface structures seen in visible light, Senseye has developed a method of projecting iris masks formed on IR images onto the data extracted from visible light. This technique uses a generative adversarial network (GAN) to predict the IR image of an input image captured under visible light (see FIG. 14). The CV mask is then run on the predicted IR image and overlaid back to the visible light image (see FIG. 15).

Figure 14:
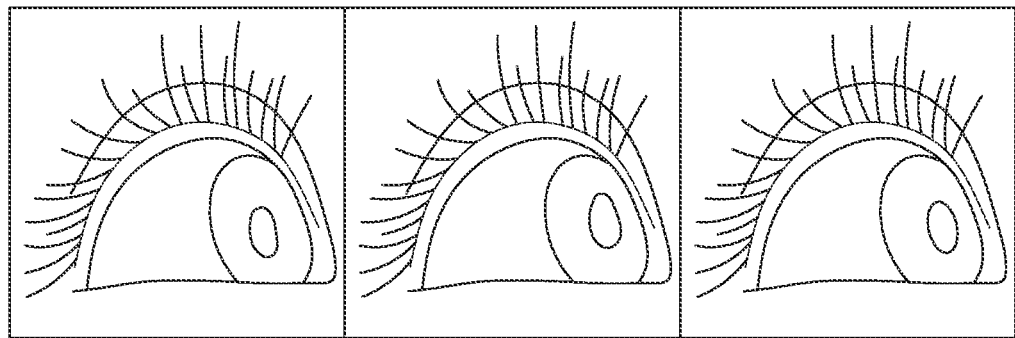
FIG. 14 is an example of GAN generation of IR image for dark eye where the generated IR image is used to create the CV mask which is then projected onto the visible light image in real time.
Figure 15:
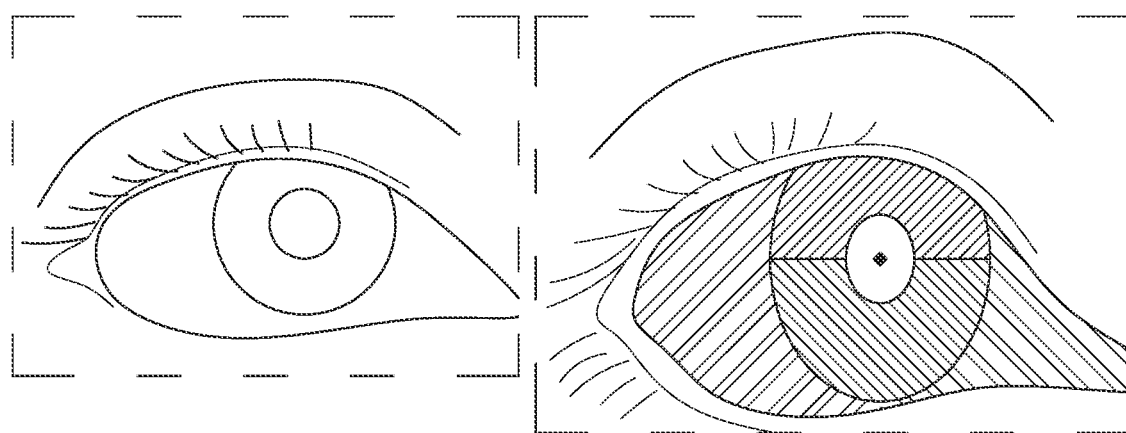
FIG. 15 is an example of the CV mask formed using the UNET prediction on the IR image and overlaid on the visible light image.

Part of this method is generating a training set of images on which the GAN learns to predict IR images from visible light images (see FIG. 14). Senseye has developed a hardware system and experimental protocol for generating these images. The apparatus consists of two cameras, one color sensitive, and one NIR sensitive (see numerals 16.1 and 16.2 in FIG. 16). The two are placed tangent to one another such that a hot mirror forms a 45 degree angle with both (see numeral 16.3 in FIG. 16). The centroid of the first surface of the mirror is equidistant from both sensors. Visible light passes straight through the hot mirror onto the visible sensor and NIR bounces off into the NIR sensor. As such, the system creates a highly optically aligned NIR and color image which can be superimposed pixel-for-pixel. Hardware triggers are used to ensure that the cameras are exposed simultaneously with error<1 uS.

Figure 16:
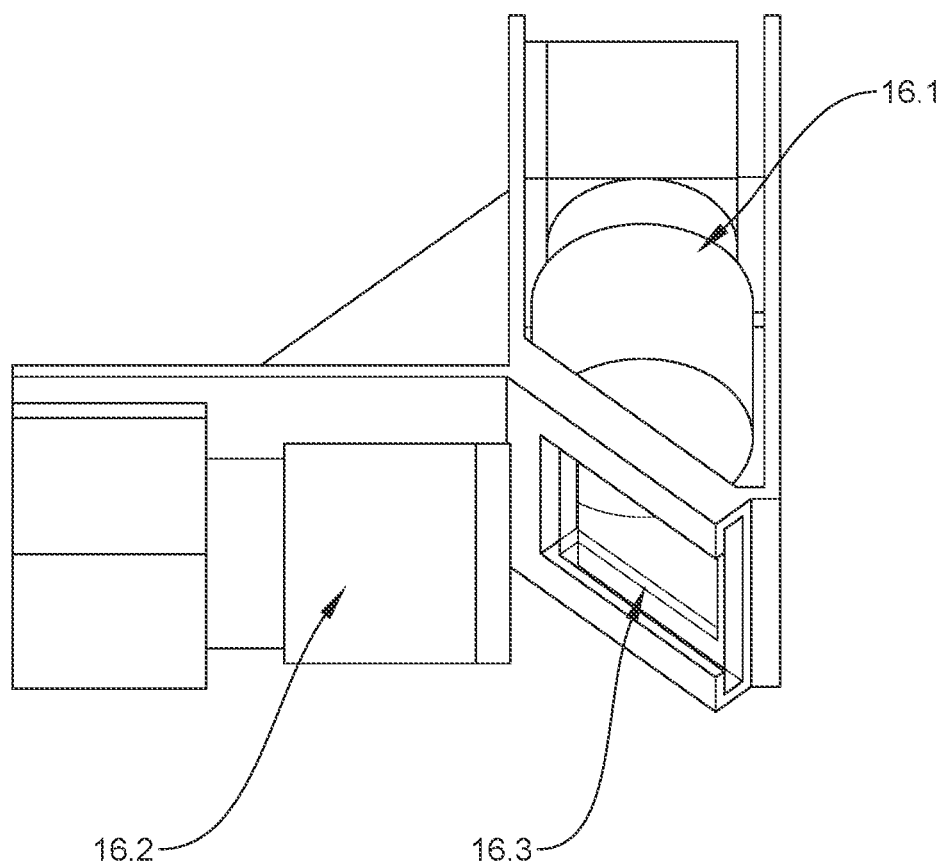
FIG. 16 is a perspective view of one embodiment of a dual camera design capturing both NIR and visible light of the same location at the same time.

FIG. 16 is a diagram of hardware design that captures NIR and visible light video simultaneously. Two cameras, one with a near IR sensor and one with a visible light sensors are mounted on a 45 degree angle chassis with a hot mirror (invisible to one camera sensor, and an opaque mirror to the other) to create image overlays with pixel-level accuracy.

Creating optically and temporally aligned visible and NIR datasets with low error allows Senseye to create enormous and varied datasets that do not need to be labelled. Instead of manual labelling, the alignment allows Senseye to use the NIR images as reference to train the color images against. Pre-existing networks already have the ability to classify and segment the eye into sclera, iris, pupil, and more, giving us the ability to use their outputs as training labels. Additionally, unsupervised techniques like pix-to-pix GANs utilize this framework to model similarities and differences between the image types. These data are used to create surface-to-surface, and/or surface-to-subsurface mapping of visible and invisible iris features.

Other methods being considered to properly filter the RGB spectrum so it resembles the NIR images, is the use of a simulation of the eye so that rendered images resembles both natural light and that in NIR light spectrum. The neural network structures would be similar to those listed previously (pix-to-pix) and the objective would be to allow for the sub cornea structures (iris and pupil) to be recovered and segmented properly despite the reflections or other artifacts caused by the interaction of the natural light spectrum (360 to 730 nm) with the particular eye.

The utility of the GAN is to learn a function that is able to generate NIR images from RGB images. The issues with RGB images derive from the degradation of contrast between pupil and iris specifically for darker eyes. What this means is that if there isn't enough light flooding the eye, the border of a brown iris and the pupil hole are indistinguishable due to their proximity in the color spectrum. In RGB space, because we do not control for a particular spectrum of light, we are at the mercy of another property of the eye which is that it acts as a mirror. This property allows for any object to appear as a transparent film on top of the pupil/iris. An example of this is you can make out a smaller version of a bright monitor on your eye given an rgb image. So the GAN acts as a filter. It filters out the reflections, sharpens boundaries, and due to its learned embedding, it is capable of restoring the true boundary of iris and pupil.

Although several embodiments have been described in detail for purposes of illustration, various modifications may be made to each without departing from the scope and spirit of the invention. Accordingly, the invention is not to be limited, except as by the appended claims.

What is claimed is:

1. A method to optimize learning based upon ocular information of a subject, the method comprising the steps of:
providing a video camera configured to record a close-up view of at least one eye of the subject;
providing a first electronic display configured to display a plurality of educational subject matter to the subject;
providing a second electronic display configured to display an output to an instructor;
providing a computing device electronically connected to the video camera, the first electronic display and the second electronic display;
recording, via the video camera, the ocular information of the at least one eye of the subject while learning the plurality of educational subject matter;
processing, via the computing device, the ocular information to identify changes in ocular signals of the subject through the use optimized algorithms;
providing a cognitive state model configured to determine a low to a high cognitive load experienced by the subject, the cognitive load measuring the extent to which the subject is drawing on mental resources;
evaluating, via the computing device, the cognitive state model based on the changes in the ocular signals and determining a probability of the low to the high cognitive load experienced by the subject; and
displaying, via the second electronic display, the probability of the low to the high cognitive load experienced by the subject to the instructor.

2. The method to optimize learning of claim 1, including the steps of, via the computing device, establishing a location of the first electronic display in relation to the at least one eye of the subject; determining from the changes in ocular signals a subject's gazing location in relation to the plurality of educational subject matter; linking the subject's gaze location of the plurality of the educational subject matter and the changes in ocular signals to the subject's cognitive load; and displaying, via the second electronic display to the instructor, the subject's cognitive load in relation to the plurality of educational subject matter.

3. The method to optimize learning of claim 1, including the step of isolating a pupil dilation of the subject resulting from changes in cognitive load from changes in ambient luminance by utilizing a power spectral density frequency transformation.

4. The method to optimize learning of claim 1, including the steps of providing an optimal learning scale model having a learning scale for the subject based upon a representative population or a subject's prior data, the learning scale ranging from under stimulated to overwhelmed; evaluating, via the computing device, the changes in ocular signals to determine the subject's position along the learning scale; and displaying, via the second display to the instructor, the subject's position along the learning scale.

5. The method to optimize learning of claim 1, including the steps of providing a memory formation model configured to determine a strength of short-term and/or long-term memories; evaluating, via the computing the device, the changes in ocular signals to determine the subject's strength of the short-term and/or the long-term memories in relation to the plurality of educational subject matter; and displaying, via the second display to the instructor, the subject's strength of the short-term and/or the long-term memories in relation to the plurality of educational subject matter.

6. The method to optimize learning of claim 1, wherein the changes in ocular signals comprise any of the following: eye movement, gaze location X, gaze location Y, saccade rate, saccade peak velocity, saccade average velocity, saccade amplitude, fixation duration, fixation entropy (spatial), gaze deviation (polar angle), gaze deviation (eccentricity), re-fixation, smooth pursuit, smooth pursuit duration, smooth pursuit average velocity, smooth pursuit amplitude, scan path (gaze trajectory over time), pupil diameter, pupil area, pupil symmetry, velocity (change in pupil diameter), acceleration (change in velocity), jerk (pupil change acceleration), pupillary fluctuation trace, constriction latency, dilation duration, spectral features, iris muscle features, iris muscle group identification, iris muscle fiber contractions, iris sphincter identification, iris dilator identification, iris sphincter symmetry, pupil and iris centration vectors, blink rate, blink duration, blink latency, blink velocity, partial blinks, blink entropy (deviation from periodicity), sclera segmentation, iris segmentation, pupil segmentation, stroma change detection, eyeball area (squinting), deformations of the stroma, iris muscle changes.

7. The method to optimize learning of claim 1, wherein the step of recording, via the video camera, the ocular information of the at least one eye of the subject while learning the plurality of educational subject matter also includes recording, via the camera, a facial expression and/or a posture of the subject while learning the plurality of educational subject matter.

* * * * *